United States Patent [19]

O'Brien et al.

[11] Patent Number: 4,576,922

[45] Date of Patent: Mar. 18, 1986

[54] HIGH EXPANSION DENTAL CROWN CORE CERAMIC COMPOSITION

[75] Inventors: William J. O'Brien; Matthew T. O'Brien, both of Ann Arbor, Mich.

[73] Assignee: The Regents of the University of Michigan, Ann Arbor, Mich.

[21] Appl. No.: 690,400

[22] Filed: Jan. 9, 1985

Related U.S. Application Data

[63] Continuation-in-part of Ser. No. 440,799, Jan. 5, 1983, abandoned.

[51] Int. Cl.$^4$ ............................................. C03C 14/00
[52] U.S. Cl. ..................................... 501/32; 106/35; 501/59; 501/77; 501/79
[58] Field of Search ............................ 510/32; 106/35

[56] References Cited

U.S. PATENT DOCUMENTS

| | | | |
|---|---|---|---|
| 2,897,595 | 8/1959 | Lee | 501/54 |
| 2,980,998 | 4/1961 | Coleman et al. | 501/135 |
| 3,069,773 | 12/1962 | Saffir | 501/38 |
| 3,504,437 | 4/1970 | Siegel | 501/135 |
| 3,649,732 | 3/1972 | Brigham et al. | 106/35 |
| 4,101,330 | 7/1978 | Burk et al. | 501/143 |
| 4,265,669 | 5/1981 | Starline et al. | 501/153 |

FOREIGN PATENT DOCUMENTS

| | | | |
|---|---|---|---|
| 57-183361 | 11/1982 | Japan . | |
| 686246 | 1/1953 | United Kingdom | 501/135 |
| 1105111 | 3/1968 | United Kingdom | 106/35 |
| 2080281 | 2/1982 | United Kingdom | 106/35 |

Primary Examiner—Helen M. McCarthy
Attorney, Agent, or Firm—Head, Johnson & Stevenson

[57] ABSTRACT

A strong white ceramic composition and method of making the same wherein said composition is characterized by an average coefficient of thermal expansion over the range of 25° C. to 500° C. ("Proposed American National Standards Institute/American Dental Association Specification No. 38.1 For Porcelain-Alloy Systems") of between 14 to $16 \times 10^{-6}$/°C. and a transverse strength of about 18,000 psi or even greater. The ceramic composition comprises about 40 to 60% by weight crystalline magnesium oxide particles (e.g., 74 μm) dispersed in a modified silicate glass containing at least 3% by weight of dissolved $ZrO_2$, $TiO_2$ or mixtures thereof and is made by firing a powdered mixture of $MgO_2$ and modified silicate glass at about 1150° C. for sufficient time to produce a fine dispersion of forsterite ($Mg_2SiO_4$) in the continuous glass matrix phase along with the crystalline magnesia particles. Such ceramic compositions are useful in high expansion dental crown core applications.

6 Claims, No Drawings

HIGH EXPANSION DENTAL CROWN CORE CERAMIC COMPOSITION

CROSS-REFERENCE TO RELATED APPLICATIONS

This application is a File Wrapper Continuation-in-Part of U.S. patent application Ser. No. 440,799 filed Jan. 5, 1983, which is now abandoned.

BACKGROUND OF THE INVENTION

1. Field of the Invention

This invention relates to ceramics and more specifically to the field of dental porcelains used to fabricate artificial teeth.

2. Description of the Prior Art

Prior ceramic=glass composite materials used in the construction of artificial teeth are characterized by a microstructure containing a crystalline ceramic in a vitreous matrix. Thus, it is known that aluminous ceramic materials contain 40 to 50% alumina in a borosilicate glass matrix. Upon firing, the resulting ceramic body has a microstructure consisting of crystalline alumina dispersed in a glass matrix. The fired alumina composite body has a diametral tensile strength of around 9,000 psi and a coefficient of thermal expansion of $8 \times 10^{-6}/°C$. In British Pat. No. 1.105,111, magnesium aluminate spinel-glass composites have also been used in the construction of artificial teeth. The raw material for this ceramic contains a mixture of alumina and a smaller amount of magnesia present in a ratio suitable for the formation of magnesium aluminate spinel and unreacted alumina. The fired ceramic body microstructure consists of magnesium aluminate and alumina crystalline phases in an alkaline earth silicate glass matrix. In U.S. Pat. No. 4,265,669, a fired magnesium aluminate-glass composite has a tensile strength of 9,000 psi and a coefficient of thermal expansion below $8 \times 10^{-6}/°C$. Both of these prior art ceramic core materials are unsuitable for bonding to high expansion dental porcelains due to the danger of cracking produced by thermal stresses because the coefficient of thermal expansion difference tolerance for bonding ceramics to porcelain is less than 100%. Since the coefficient of thermal expansion of high expansion feldspar porcelains range from range from 12 to $14 \times 10^{-6}/°C$., the prior art ceramics described above are unuitable for bonding to feldspar porcelains. The prior art ceramics can only be used for bonding to low expansion dental porcelains. This is a serious disadvantage since dental laboratories have the high expansion porcelains available for use in the construction of porcelain fused to metal dental crown and bridgework.

SUMMARY OF THE INVENTION

In view of the limitations of the prior art compositions associated with their low coefficient of thermal expansion, the present invention provides a strong, white ceramic material with a coefficient of thermal expansion of between 14 and $16 \times 10^{-6}/°C$. suitable for bonding to high expansion porcelains with significantly higher strength. The ceramic compositions of the present invention are capable of forming a strong ceramic-glass composite body with special application as an inner reinforcing core in the construction of artificial teeth with high expansion dental porcelains.

Thus, the present invention provides a ceramic composition characterized by a coefficient of thermal expansion in the temperature range from 25° C. to 500° C. of between about $14 \times 10^{-6}/°C$. to about $16 \times 10^{-6}/°C$. and further characterized by a transverse strength of about 18,000 psi or greater comprising from about 40 to 60% by weight of a finely ground, magnesium oxide dispersed in silicate glass matrix containing at least 3% by weight of zirconium oxide, titanium oxide, or mixtures thereof.

The method of making the corresponding ceramic composition according to the present invention comprises the steps of:

(a) mixing from about 40 to 60 parts by weight of a finely ground, magnesium oxide with a corresponding 60 to 40 parts by weight, respectively, of a modified silicate glass containing at least about 3% by weight zirconium oxide, titanium oxide or mixtures thereof;

(b) firing the mixture produced in step (a) at about 1150° C. for sufficient time to produce crystalline magnesium oxide particles dispersed in a matrix consisting of a glass phase containing a fine dispersion of forsterite;

(c) cooling the fired mixture produced in step (b); and (d) recovering the resulting tough, high coefficient of thermal expansion, ceramic composition.

The higher strength and more consistent thermal expansion properties are achieved by dispersion strengthening and chemical bonding between the magnesium oxide and the glass matrix of the fired ceramic body. Dispersion strenghtening is produced by incorporating 40-60% of magnesium oxide in a glass matrix which acts to reduce the size of Griffith flaws. The strengthening is further increased by incorporating at least 3% of dissolved titanium oxide or of zirconium oxide or a mixture of both in the glass component of the raw material mixture. When the magnesium oxide is fired with the titania or zirconia glasses to around 1150° C., a reaction occurs at the magnesium oxide-glass interface to produce magnesium-titanium or magnesium-zirconium compounds. This chemical bonding at the interface (more specifically chemical bonding between the final crystalline magnesia particle and the surrounding vitreous glass phase) results in an increase of the diametral tensile strength to 12,500 psi and higher thermal expansion values. These properties are further enhanced by the formation of finely dispersed forsterite in the vitreous matrix. The prior art ceramics described above have relied upon weaker physical bonding between the dispersed crystalline phases and the glass matrix. Matching of the coefficient of thermal expansion of the magnesium oxide with a glass having a slightly lower value also prevents weakening of the bonds achieved due to internal thermal stresses.

It is an object of the present invention to provide a ceramic composition characterized by a coefficient of thermal expansion more closely analogous to the coefficient of thermal expansion of the contemporary high expansion dental porcelains. It is another object of the present invention to provide such a high expansion ceramic composition with improved tensile strength. It is a further object of the present invention to provide a method of making such strength, high expansion ceramic compositions and using them as a dehtal crown core. Fulfillment of these objects and the presence and fulfillment of additional objects will become apparent upon complete reading of the specification and claims.

DESCRIPTION OF THE PREFERRED EMBODIMENTS

In order to achieve the objects of the present invention, a powdered mixture of magnesium oxide and glass frit are reacted. Preferably, the powdered mixture involves a 200 mesh (Tyler) blend of 40 to 60 weight % crystalline magnesium oxide in combination with a modified silicate glass containing at least 3 weight % dissolved zirconium oxide, titanium oxide or mixture thereof. The glass frit should have a coefficient of thermal expansion of between 9 to $12 \times 10^{-6}/°C$. The optimum reaction temperature is approximately 1150° C. and is preferably followed by a quenching in water. The resulting product of the reaction can then be ground to about 400 mesh (Tyler) to form the ceramic raw material useful for joining to dental body porcelains. Upon firing the powdered reaction product to the 1150° C. in the normal dental porcelain furnace procedures under vacuum and cooling, a ceramic with microstructure containing crystalline magnesium oxide particles dispersed in a matrix consisting of a glass phase containing a fine dispersion of forsterite ($Mg_2SiO_4$) is produced. A high transverse strength approaching 20,000 psi is do, in part, to the dispersion strengthening of the magnesium oxide particles and, in part, to the fine forsterite crystals dispersed in the matrix phase. An unexpectedly high coefficient of thermal expansion approaching 14 to $16 \times 10^{-6}/°C$. as measured by a single push dilatometer according to methods used for dental porcelains is do to an unpredicted thermal expansion that takes place between about 300° and 500° C. This high coefficient of thermal expansion in turn facilitates the thermal compatibility between the ceramic compositions of the present invention and prior art dental porcelains having high thermal expansion coefficients (see for example, Whitlock, et al, "Consideration of Some Factors Influencing Compatibility of Dental Porcelains and Alloys, Part I: Thermal-Physical Properties", Porc. 4th Int'l. Precious Metals, Conference, Pergamon, Canada, 1980).

The following examples are presented to further illustrate the compositions according to the present invention and how they are made.

EXAMPLE 1

Forty grams of 200 mesh Tyler crystalline magnesium oxide was mixed with 60 grams of a ground glass frit with a measured coefficient of thermal expansion (25°-500° C. ) of $9 \times 10^{-6}/°C$. and a composition as follows:

|  | Weight Percent |
|---|---|
| $SiO_2$ | 58.00 |
| $Al_2O_3$ | 1.50 |
| $TiO_2$ | 5.00 |
| $ZrO_2$ | 6.00 |
| $Na_2O$ | 10.00 |
| $K_2O$ | 5.00 |
| $B_2O$ | 9.50 |
| F | 5.00 |

The above mixture was then heated to 1150° for 15 minutes, quenched in water and ground to 400 mesh. Ten 2 cm transverse strength and 5 cm thermal expansion specimens were prepared by compacting in a mold and firing to 1120° C. under vacuum in a Ney Dental Porcelain furnace. The average transverse strength measured in 3 point loading was found to be 20,000 psi.

The coefficient of thermal expansion in the range 25° C. to 500° C. was found to be $15 \times 10^{-6}/°C$. Since the coefficient of thermal expansion of magnesium oxide has a reported value of $13.5 \times 10^{-6}/°C$. (Kingery, W. D. et. al., Introduction to Ceramics, 2nd ed. Wiley, P. 595, 1976), and the glass had a measured value of $9 \times 10^{-6}/°C$., the value of the combination at $16 \times 10^{-6}/°C$. was higher than expected.

EXAMPLE 2

Fifty grams of 200 mesh Tyler crystalline magnesium oxide was mixed with 50 grams of a ground glass with a measured coefficient of thermal expansion (25°-500° C.) of $10 \times 10^{-6}/°C$. and a composition as follows:

|  | Weight Percent |
|---|---|
| $SiO_2$ | 28.5 |
| $Al_2O_3$ | 7.0 |
| CaO | 5.0 |
| $ZrO_2$ | 13.0 |
| $Na_2O$ | 13.5 |
| $B_2O_3$ | 18.0 |
| ZnO | 3.5 |
| $P_2O_5$ | 2.5 |
| F | 9.0 |

The above mixture was heated to 1150° C., quenched in water and ground to 400 mesh. Ten 2 cm transverse strength and 5 cm thermal expansion specimens were prepared by compacting in a mold and firing to 1120° C. under vacuum. The average transverse strength measured in 3 point loading was found to be 18,000 psi. The coefficient of thermal expansion was measured with a dilatormeter and found to be $14 \times 10^{-6}/ °C$.

EXAMPLE 3

40 grams of $-200$ mesh Tyler magnesium oxide was mixed with 60 grams of a ground glass frit with the following composition:

|  | Weight Percent |
|---|---|
| $SiO_2$ | 60 |
| $TiO_2$ | 6 |
| $B_2O_3$ | 4 |
| $Al_2O_3$ | 3 |
| CaO | 3 |
| $Na_2O$ | 22 |
| F | 2 |

EXAMPLE 4

50 grams of $-200$ mesh Tyler magnesium oxide was mixed with 50 grams of a ground glass frit with the following composition:

|  | Weight Percent |
|---|---|
| $SiO_2$ | 35 |
| $ZrO_2$ | 8 |
| $TiO_2$ | 5 |
| $B_2O_3$ | 20 |
| $Al_2O_3$ | 5 |
| CaO | 5 |
| $Na_2O$ | 20 |
| F | 2 |

The above mixture was heated to 1150° C. for 30 minutes, cooled and ground to a $-200$ mesh powder. The reacted powder was then mixed with 10 percent by weight of a finely ground silica glass to form a dental porcelain suitable for the fabrication of artificial teeth.

To further evaluate the unexpected high coefficient of thermal expansion associated with the compositions according to the present invention, a thermal expansion curve involving the observed relative displacement (i.e, thermal expansion Δ1/1) was measured from room temperature to approximately 850° C. This displacement data when plotted as a function of temperature revealed an unexpected break in the slope between ≃300° and 500° C. corresponding to an unpredicted thermal expansion. This additional thermal expansion and resulting higher average coefficient of thermal expansion is felt to facilitate the thermal compatibility of the compositions of the present invention with contemporary high expansion porcelains compositions and thus alleviate the prior art problems associated with dissimilar expansion rates when making dental crowns and bridgework.

It is contemplated that the compositions according to the present invention can be employed in any of the methods and process for making dental crowns and bridgeworks as generally known in the art wherein bonding of two or more high expansion material is present. In particular the composition are useful as dental crown core ceramic compositions. It should be further appreciated that various additional additives can be present, particularly in the glass matrix phase, again as generally known and taught in the art.

Having thus described the preferred embodiments of the invention with a certain degree of particularity, it is to be recognized and understood that many changes can be made in the details of preparing and using the high expansion ceramic compositions without departing from the spirit and scope of this disclosure. Therefore, it is to be understood that the invention is not limited to the embodiments set forth herein for purposes of exemplifications, but is to be limited only by the scope of the attached claims including a full range of equivalents to which each element thereof is entitled.

We claim:

1. A ceramic composition characterized by a coefficient of thermal expansion in the temperature range from 25° C. to 500° C. of between about $14 \times 10^{-6}/°C$. to about $16 \times 10^{-6}/°C$. and further characterized by a transverse strength of about 18,000 psi or greater comprising from about 40 to 60% by weight of a finely ground, magnesium oxide dispersed in silicate glass matrix containing at least 3% by weight of zirconium oxide, titanium oxide, or mixtures thereof.

2. A ceramic composition of claim 1 wherein said finely ground, magnesium oxide and said silicate glass matrix containing at least 3% by weight zirconium oxide, titanium oxide or mixtures thereof was obtained after being fired to about 1150° C. resulting in crystalline magnesium oxide particles dispersed in a matrix consisting of a glass phase containing a fine dispersion of forsterite.

3. A ceramic composition of claim 2 wherein said crystalline magnesium oxide particles are less than about 74 μm in diameter.

4. A method of making a ceramic composition characterized by a coefficient of thermal expansion in the temperature range of from 25° C. to 500° C. of between $14 \times 10^{-6}/°C$. to about $16 \times 10^{-6}/°C$. and further characterized by a transverse strength of about 18,000 psi or greater comprising the steps of:

(a) mixing from about 40 to 60 parts by weight of a finely ground, magnesium oxide with a corresponding 60 to 40 parts by weight, respectively, of a modified silicate glass containing at least about 3% by weight zirconium oxide, titanium oxide or mixtures thereof said glass having a coefficient of thermal expansion between 9 to $12 \times 10^{-6}/°C$.;

(b) firing said mixture produced in step (a) at about 1150° C. for sufficient time to produce crystalline magnesium oxide particles dispersed in a matrix consisting of a glass phase containing a fine dispersion of forsterite;

(c) cooling said fired mixture produced in step (b); and (d) recovering said resulting tough, high coefficient of thermal expansion, ceramic composition.

5. A method of claim 4 wherein said firing is performed in vacuum.

6. A method of claim 5 wherein said cooling is by quenching in water.

* * * * *